(12) United States Patent
Simon

(10) Patent No.: US 9,326,737 B2
(45) Date of Patent: May 3, 2016

(54) METHOD AND SYSTEM FOR PROVIDING INJURY-BASED PARTICIPATION MANAGEMENT FOR TEAM ACTIVITIES

(71) Applicant: Verizon Patent and Licensing Inc., Basking Ridge, NJ (US)

(72) Inventor: Adam J. Simon, Keller, TX (US)

(73) Assignee: VERIZON PATENT AND LICENSING INC., Basking Ridge, NJ (US)

( * ) Notice: Subject to any disclaimer, the term of this patent is extended or adjusted under 35 U.S.C. 154(b) by 228 days.

(21) Appl. No.: 14/138,711

(22) Filed: Dec. 23, 2013

(65) Prior Publication Data
US 2015/0173669 A1 Jun. 25, 2015

(51) Int. Cl.
*A61B 5/00* (2006.01)
*G06F 19/00* (2011.01)
*A61B 5/11* (2006.01)
*A42B 3/04* (2006.01)

(52) U.S. Cl.
CPC .............. *A61B 5/7475* (2013.01); *A61B 5/0022* (2013.01); *A61B 5/1121* (2013.01); *A61B 5/4064* (2013.01); *A61B 5/4076* (2013.01); *A61B 5/6803* (2013.01); *A61B 5/6898* (2013.01); *A61B 5/7465* (2013.01); *G06F 19/345* (2013.01); *G06F 19/3431* (2013.01); *A42B 3/046* (2013.01); *A61B 5/7282* (2013.01); *A61B 2505/09* (2013.01)

(58) Field of Classification Search
CPC .......... A61B 5/11; A61B 5/16; A61B 5/4064; A61B 5/6803; A61B 5/6814; A61B 3/0083; A61B 3/032; A61B 3/113; A61B 5/0022; A61B 5/1121; A61B 5/7475; A63B 2220/50; A63B 2220/53; A42B 3/046
See application file for complete search history.

(56) References Cited

U.S. PATENT DOCUMENTS

| | | | | |
|---|---|---|---|---|
| 5,621,922 A | * | 4/1997 | Rush, III ................ | A42B 3/046 2/422 |
| 6,826,509 B2 | * | 11/2004 | Crisco, III .............. | A42B 3/046 2/422 |
| 8,548,768 B2 | * | 10/2013 | Greenwald .......... | A61B 5/0002 340/573.1 |
| 8,764,532 B1 | * | 7/2014 | Berme .................... | A61B 5/742 434/258 |
| 8,808,179 B1 | * | 8/2014 | Cinberg ................. | A61B 3/113 351/209 |
| 8,981,952 B2 | * | 3/2015 | Howard ................ | A42B 3/046 2/10 |
| 9,076,041 B2 | * | 7/2015 | Bentley .................... | A63F 13/00 |
| 9,078,598 B2 | * | 7/2015 | French ................. | A61B 5/4088 |
| 9,101,312 B2 | * | 8/2015 | Waldorf ................. | A61B 3/032 |
| 9,131,741 B2 | * | 9/2015 | Maliszewski ............ | H04Q 9/00 |
| 9,149,227 B2 | * | 10/2015 | Benzel ................... | A61B 5/682 |

* cited by examiner

*Primary Examiner* — Max Hindenburg

(57) ABSTRACT

An approach for providing diagnostic information regarding one or more impacts sustained by one or more users while the one or more users are participating in a team activity is described. A diagnostic platform detects one or more impacts sustained by a user, wherein the user is part of a team with one or more other users engaged in a team activity. The diagnostic platform generates a recommendation for a level of participation of the user, the one or more other users, or a combination thereof in the team activity based on the one or more impacts, a severity level of the one or more impacts, or a combination thereof. The diagnostic platform further presents the recommendation, a representation of the severity level, a representation of the level of participation, or a combination thereof in a user interface.

20 Claims, 11 Drawing Sheets

US 9,326,737 B2

METHOD AND SYSTEM FOR PROVIDING INJURY-BASED PARTICIPATION MANAGEMENT FOR TEAM ACTIVITIES

BACKGROUND INFORMATION

Application developers and service providers are continually challenged to deliver value and convenience to consumers by providing compelling applications and delivery platforms. One area of interest has been the development of applications and/or services that can enable coaches, medical personnel (e.g., clinicians, trainers, etc.), and/or users alike to diagnose and to monitor the effects of a mild traumatic brain injury or a concussion sustained by a user while he or she is participating in a physical activity such as football, baseball, hockey, lacrosse, etc. (e.g., sustaining a concussion while being tackled). However, many of today's applications and/or services are individually focused and do not take into consideration both the short-term and long-term effects of such injuries (e.g., over the length of a season).

Based on the foregoing, there is a need for providing diagnostic information regarding one or more impacts sustained by one or more users while the one or more users are participating in a team activity.

BRIEF DESCRIPTION OF THE DRAWINGS

Various exemplary embodiments are illustrated by way of example, and not by way of limitation, in the figures of the accompanying drawings in which like reference numerals refer to similar elements and in which.

DESCRIPTION OF THE PREFERRED EMBODIMENT

An apparatus, method and software for providing diagnostic information regarding one or more impacts sustained by one or more users while the one or more users are participating in a team activity. In the following description, for the purposes of explanation, numerous specific details are set forth in order to provide a thorough understanding of the present invention. It is apparent, however, to one skilled in the art that the present invention may be practiced without these specific details or with an equivalent arrangement. In other instances, well-known structures and devices are shown in block diagram form in order to avoid unnecessarily obscuring the present invention.

Figure 1:
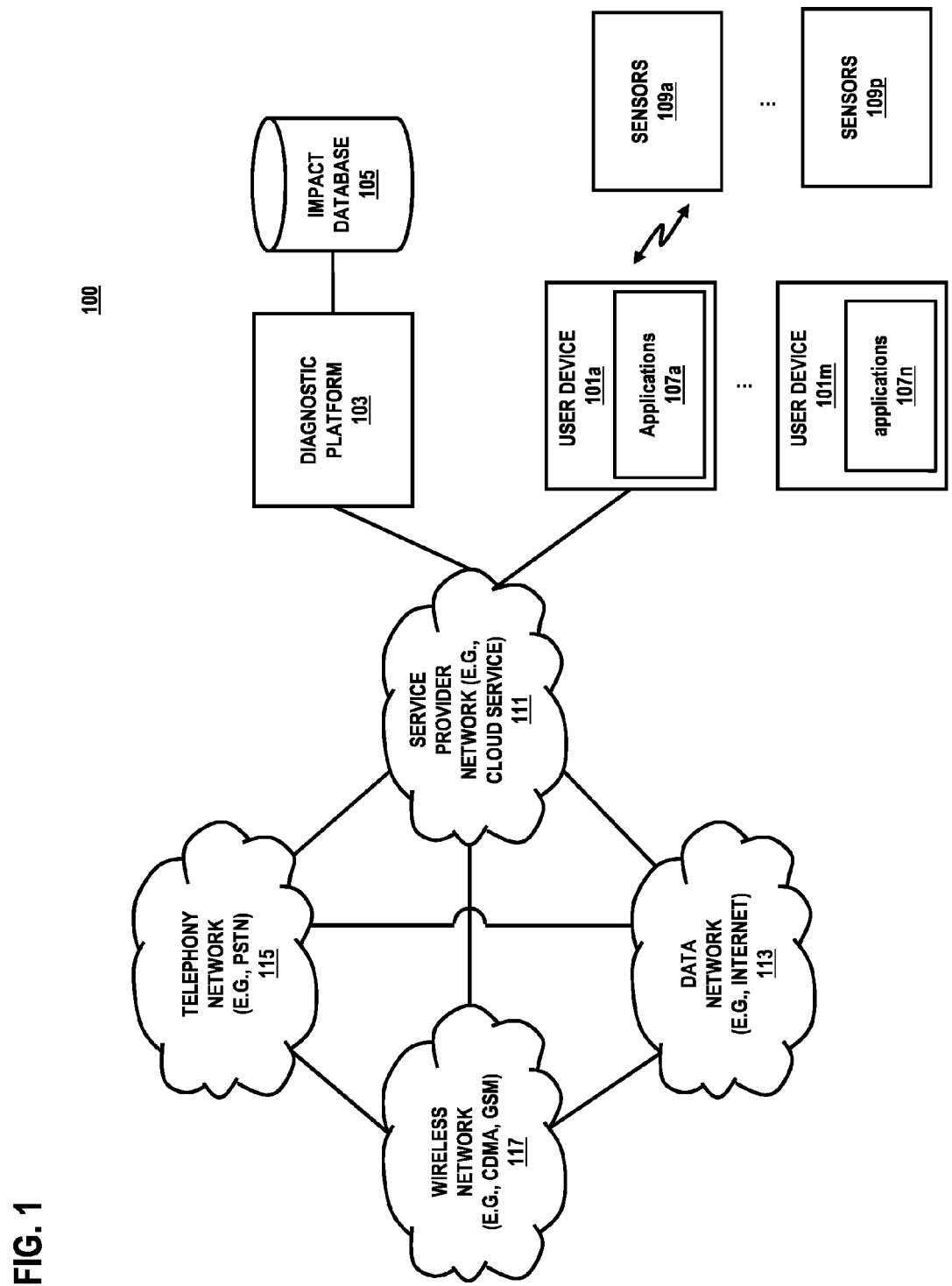
FIG. 1 is a diagram of a system for providing diagnostic information regarding one or more impacts sustained by one or more users while the one or more users are participating in a team activity, according to one embodiment.

FIG. 1 is a diagram of a system for providing diagnostic information regarding one or more impacts sustained by one or more users while the one or more users are participating in a team activity, according to one embodiment. As previously discussed, there is increasing interest among application developers and services providers to provide applications and/or services that can enable coaches, medical personnel (e.g., clinicians, trainers, etc.), and/or users alike to diagnose and to monitor the effects of mild traumatic brain injury sustained by a user while he or she is participating in a physical activity such as football, baseball, hockey, lacrosse, etc. (e.g., sustaining a concussion from a tackle or from a ball or puck striking one's head, etc.). However, many of today's applications and/or services are individually focused and do not take into consideration both the short-term and long-term effects of such injuries. For example, such applications do not take into consideration one or more impacts across an entire season.

To address this problem, a system 100 introduces the capability to provide diagnostic information regarding one or more impacts sustained by one or more users while the one or more users are participating in a team activity, according to one embodiment. For the purpose of illustration, the system 100 that enables a coach, medical personnel, or a user to view diagnostic information regarding one or more impacts sustained by a user while he or she is participating in a team activity via one or more user devices 101*a*-101*m* (e.g., a mobile phone, a phablet, and/or a tablet)(also referred to collectively as user devices 101) is described with respect to a diagnostic platform 103. In one embodiment, the diagnostic platform 103 may include or be associated with an impact database 105. In one example embodiment, the diagnostic platform 103 may exist in whole or in part within a user device 101, or independently and the impact database 105 may exist in whole or in part within the diagnostic platform 103. By way of example, the impact database 105 may include the number and the severity level of one or more impacts sustained by one or more users on a team over a period of time (e.g., one or more seasons), biometric data and/or contextual data associated with the one or more users (e.g., height, weight, medical history, location where the impact occurred, etc.), contextual data associated with the team (e.g., date, temperature, time, types of activities, location on a field where one or more impacts occurred, etc.), or a combination thereof. The impact database 105 may also include one or more recommendations for a level of participation for the user, the one or more users, or a combination thereof in the team activity based on the one or more impacts, a severity level of the one or more impacts, or a combination thereof. For example, a recommendation may state "remove the user for the rest of the game," "carefully monitor the user's performance for a period of time," "examine the user for possible signs of a concussion," "the user is safe to participate and/or to continue participating," etc.

In one embodiment, the user devices 101 also include or have access to one or more applications 107*a*-107*n* (also collectively referred to as applications 107). By way of example, the applications 107 may include one or more health-based applications (e.g., brain monitoring applications, fitness level applications, etc.), one or more activity-based applications (e.g., lineup or formation applications, stamina levels, scouting reports, etc.), one or more context-based applications (e.g., weather conditions, field conditions, etc.). In addition, the user devices 101 are associated with one or more sensor devices 109*a*-109*p* (also collectively referred to as sensor devices 109)(e.g., a sensor-based helmet and/or a sensor-based mouth guard). By way of example, the sensor-based helmet or mouth guard may include a g-force sensor, a vibration sensor, an accelerometer, a gyroscope, or a combination thereof. In one embodiment, it is contemplated that the user devices 101 and the sensor devices 109 may function and/or communicate together via one or more short-range wireless communications including Bluetooth®, near field communication (NFC), or a combination thereof.

As seen in FIG. 1, the user devices 101, the diagnostic platform 103, the impact database 105, the applications 107, the sensor devices 109 and other elements of the system 100 may be configured to communicate via a service provider network 111 (e.g., a cloud service). According to certain embodiments, one or more networks, such as data network 113, telephony network 115, and/or wireless network 117, can interact with the service provider network 111. Networks 111-117 may be any suitable wireline and/or wireless network, and be managed by one or more service providers. For example, telephony network 115 may include a circuit-switched network, such as the public switched telephone network (PSTN), an integrated services digital network (ISDN), a private branch exchange (PBX), or other like network.

Networks 111-117 may employ various technologies for enabling wireless communication including, for example, code division multiple access (CDMA), long term evolution (LTE), enhanced data rates for global evolution (EDGE), general packet radio service (GPRS), mobile ad hoc network (MANET), global system for mobile communications (GSM), Internet protocol multimedia subsystem (IMS), universal mobile telecommunications system (UMTS), etc., as well as any other suitable wireless medium, e.g., microwave access (WiMAX), wireless fidelity (Wi-Fi), satellite, and the like. Meanwhile, data network 113 may be any local area network (LAN), metropolitan area network (MAN), wide area network (WAN), the Internet, or any other suitable packet-switched network, such as a commercially owned, proprietary packet-switched network, such as a proprietary cable or fiber-optic network.

Still further, the communication provider network may embody circuit-switched and/or packet-switched networks that include facilities to provide for transport of circuit-switched and/or packet-based communications. It is further contemplated that networks 111-117 may include components and facilities to provide for signaling and/or bearer communications between the various components or facilities of system 100. In this manner, the communication networks 111-117 may embody or include portions of a signaling system 7 (SS7) network, Internet protocol multimedia subsystem (IMS), or other suitable infrastructure to support control and signaling functions.

It is noted that the user devices 101 may be any type of mobile terminal, fixed terminal, or portable terminal including a mobile handset, station, unit, device, multimedia computer, multimedia tablet, Internet node, communicator, desktop computer, laptop computer, Personal Digital Assistants (PDAs), smartphone or any combination thereof. It is also contemplated that the user devices 101 can support any type of interface for supporting the presentment or exchanging of data. In addition, the user devices 101 may facilitate various input means for receiving and generating information, including touch screen capability, keyboard and keypad data entry, voice-based input mechanisms and the like. Any known and future implementations of user devices 101 are applicable.

In one embodiment, the system 100 monitors biometric data, contextual data, or a combination thereof associated with a user, one or more users, a team, a team activity, or a combination thereof. By way of example, the biometric data may include the height, weight, athletic condition, etc. of one or more users. By way of further example, the contextual data may include the medical history of a user (e.g., any pre-existing conditions, one or more previously sustained impacts, etc.), an amount of elapsed time since previously sustaining one or more impacts, weather conditions (e.g., temperature, rain, snow, etc.), drills or plays where one or more impacts are likely (e.g., tackling drills), specific positions within an activity (e.g., a running back versus a quarterback in football), one or more locations on the body where the one or more impacts have been sustained, etc. In one embodiment, it is contemplated that a user, a coach, or medical personnel (e.g., a clinician, a trainer, etc.) can input the biometric data, contextual data, or a combination thereof into the system 100 via a user device 101, for example, before the user starts participating in a team activity and thereby establishing one or more baseline values for the user; during the team activity to monitor any changes; or a combination thereof. In one embodiment, depending on the sophistication of the user devices 101, the sensor devices 109, or a combination thereof, it is contemplated that some of the contextual data (e.g., time and temperature) may be automatically detected by the system 100 via the networks 111-117 (e.g., a cloud service) and therefore not require manual input on the part of the user, the coach, and/or the medical personnel.

In one embodiment, the system 100 detects one or more impacts sustained by a user. In particular, it is contemplated that the user is part of a team with one or more other users engaged in a team activity that is either a physical activity or a contact sport in which impact to a user's head may likely occur. By way of example, the one or more impacts may include linear, rotational, and/or angular movement of the user's brain. More specifically, the measure of the movement is detected from sensor information associated with equipment worn by the user, the one or more other users, or a combination thereof (e.g., a sensor-based helmet, a sensor-based mouth guard, or a combination thereof) and the sensor information includes, g-force data, vibration data, acceleration data, rotational data, or a combination thereof. For example, a user may be a football player that sustains a single severe impact (e.g., a mild traumatic brain injury or a concussion—knocking him or her out of the activity) or the user may sustain a number of the one or more impacts throughout the course of the activity, a season, a career, or a combination thereof. In one embodiment, it is contemplated that the system 100 can store both the number of the one or more impacts sustained by a user and the contextual data associated with the one or more impacts in the impact database 105 (e.g., the amount of time elapsed between the one or more impacts, the activity during which the one or more impacts were sustained, the area of the field where the one impacts were sustained, etc.). Consequently, the system 100 may detect that one or more users are sustaining one or more impacts during a particular drill, for example, and therefore the coach, for example, can modify the drill accordingly or discontinue the drill entirely. Similarly, the system 100 can detect that one or more users are sustaining one or more impacts while on the right side of the quarterback, for example, and therefore the coach, for example, may want to move larger/stronger users to the right side of the quarterback, if possible.

In one embodiment, the system 100 calculates the severity level for a single one, a plurality, or an entirety of the one or more impacts. By way of example, the system 100 calculates the severity level by comparing the sensor information, including g-force data, vibration data, acceleration data, rotational data, or a combination thereof against impact threshold criteria (e.g., a concussion grading system and/or clinical studies) stored in the impact database 105 and/or available via the networks 111-117 (e.g., a cloud service). For example, the system 100 can determine that a user sustained an impact consisting of a linear impact component (e.g., x number of g-forces (g's)) and/or a rotational movement or angular acceleration component (e.g., x number of radians/s$^2$) and determine that based on those values compared against the impact threshold criteria that the user has sustained a concussion.

In one embodiment, the system 100 monitors the one or more impacts sustained by the user over a period of time. By way of example, the period of time represents a duration of the team activity (e.g., a football game or practice), a duration of a season for a team activity (e.g., a football season), a duration of a career for the team activity (e.g., a quarterback's career), or a combination thereof. In particular, a user that has sustained a number of impacts over a period of time (e.g., a duration of a season) may be at the same level of risk to short-term and/or long-term injury as a user that has sustained a single severe impact even if the impacts over the period of time are minimal or moderate in severity. In addition, a user that has sustained a severe impact (e.g., a concussion) may be more susceptible to sustain another concussion from one or more impacts, particularly if the time between such one or more impacts is minimal.

In one embodiment, the system 100 generates a recommendation for a level of participation of the user, the one or more other users, or a combination thereof in a team activity based on the one or more impacts, a severity level of the one or more impacts, or a combination thereof. By way of example, the system 100 generates the recommendation by comparing the number of the one or more impacts, the calculated severity of the one or more impacts, or a combination thereof sustained by a user over a period of time (e.g., the duration of the activity or the duration of a season) against one or more corresponding recommendations stored in the impact database 105. In addition, the system 100 can generate the recommendation based on the biometric and/or contextual data associated with a user and stored in the impact database 105, for example. Further, in one embodiment, it is contemplated that the system 100 can "predict" a level of risk of short-term and/or long-term injury for a user based on the one or more impacts sustained by a user over a period of time and can then generate a recommendation for a level of participation for the user accordingly. For example, based on one or more impacts sustained by a user (e.g., user "A"), the system 100 can recommend to a coach, for example, that the user should not continue to participate in the activity for the duration of the activity, the duration of the season (e.g., if the user has already sustained a number of severe impacts over the course of the season and/or his or her career depending on the particular circumstances). In addition and alternatively, the system 100 can recommend to the coach that the user is at a moderate to high level of risk of injury and therefore should be carefully watched for a period of time (e.g., the next few plays) and/or immediately examined by medical personnel (e.g., a clinician, a trainer, etc.) for possible signs of a mild traumatic brain injury or a concussion upon sustaining one or more impacts. Further, the system 100 can also recommend that the user is safe to participate and/or to continue participating in the activity despite having sustained one or more impacts (e.g., one or more impacts of minimal severity). By way of further example, the system 100 can generate the recommendation for a level of participation for a user in substantially real-time, periodically, according to a schedule, on demand, or a combination thereof.

In one embodiment, the system 100 presents the recommendation, a representation of the severity level, a representation of the level of participation, or a combination thereof in a user interface (e.g., a user interface of a user device 101). By way of example, a coach, for example, may be holding or have a view of a user device 101 (e.g., a tablet) on which the system 100 presents a text-based recommendation of the level of participation for one or more users (e.g., "take the user off of the field for the rest of the activity," "carefully monitor the user for a period of time," "examine the user for possible signs of a concussion," "the user is safe to participate and/or to continue participating," etc.). In addition, the system 100 may also present the recommendation as an audio and/or haptic alert (e.g., a vibration immediately after a user sustains a severe impact). In the same example use case, the coach, for example, may interact with the user interface (e.g., based on one or more gestures) to view a representation of the severity of the one or more impacts sustained by a user. In one embodiment, it is contemplated that a medical professional may have access to the user interface of a user device 101 to quickly diagnose the severity of the one or more impacts (e.g., upon a user's admission to an emergency room). By way of example, the system 100 can represent the recommended level of participation based on one or more colors. For example, a user that has sustained a number of severe impacts and/or a severe impact recently may be represented with a red color, a user that has sustained a number of impacts of minimal severity may be represented as a yellow color, and a user that has not sustained any impacts or only a few impacts of minimal severity may be represented as a green color.

In one embodiment, the system 100 can determine a substitution of a user for one or more other users participating in the team activity based on the one or more impacts. By way of example, if the system detects that a user (e.g., user "A") has sustained a number of impacts throughout the course of the activity (e.g., a football game), the system 100 can suggest a substitution of user "B", for example, for user "A" during the particular activity or for a period of time (e.g., the next scheduled activity). In one embodiment, it is contemplated that the system 100 can determine the one or more substitutions based on the premise that there should be no severely impacted users (e.g., red users) participating in the activity at any given time and that the number of cautionary users (e.g., yellow users) participating in the activity should be minimized as much as possible. Therefore, if possible, the system 100 can determine the one or more substitutions so that the one or more users participating in the activity are currently safe to participate and/or to continue participating (e.g., green users).

Figure 2:
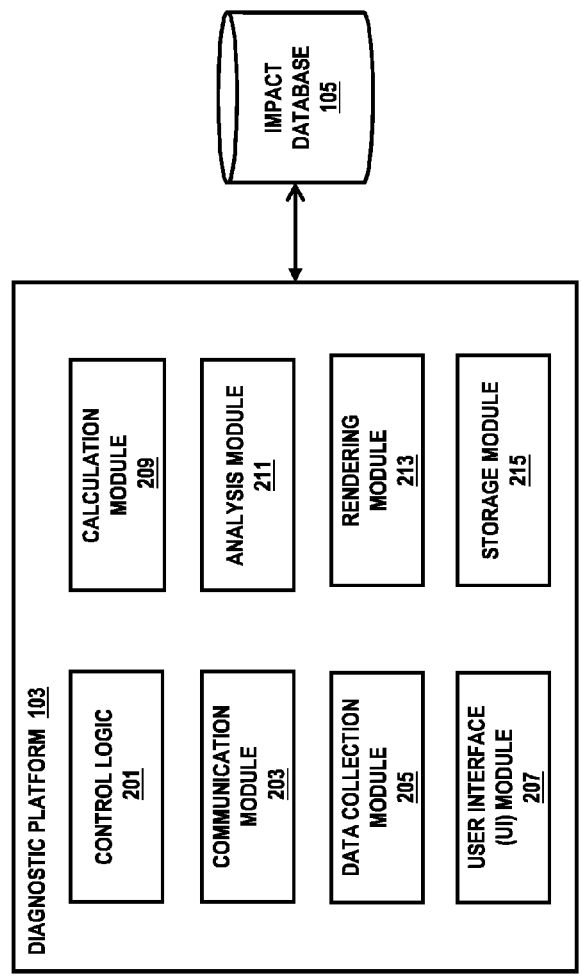
FIG. 2 is a diagram of a diagnostic platform, according to one embodiment.

FIG. 2 is a diagram of the components of the diagnostic platform 103, according to one embodiment. By way of example, the diagnostic platform 103 includes one or more components for providing diagnostic information regarding one or more impacts sustained by one or more users while the one or more users are participating in a team activity. It is contemplated that the functions of these components may be combined in one or more components or performed by other components of equivalent functionality. In this embodiment, the diagnostic platform 103 includes a control logic 201, a communication module 203, a data collection module 205, a user interface (UI) module 207, a calculation module 209, an analysis module 211, a rendering module 213, and a storage module 215.

In one embodiment, the control logic 201 oversees tasks, including tasks performed by the communication module 203, the data collection module 205, the UI module 207, the calculation module 209, the analysis module 211, the rendering module 213, and the storage module 215. For example, although the other modules may perform the actual task, the control logic 201 may determine when and how those tasks are performed or otherwise direct the other modules to perform the task.

In certain embodiments, the communication module 203 is used for communication between the user devices 101, the diagnostic platform 103, the impact database 105, the applications 107, the sensor devices 109, and the networks 111-117. In one embodiment, the communication module 203 may also be used to communicate commands, requests, data, etc.

In one embodiment, the data collection module 205, in connection with the UI module 207, is used to monitor biometric data, contextual data, or a combination thereof associated with a user, one or more users, a team, a team activity, or a combination thereof. By way of example, a coach, for example, may input biometric data (e.g., weight, height, age, etc.), contextual data (e.g., medical history information, weather or temperature conditions, etc.), or a combination thereof associated with a user to the diagnostic platform 103 via a keypad or one or more voice recognition capabilities associated with a user device 101. Once inputted, the data collection module 205, in connection with the storage module 215, can collect and organize the data. The data collection module 205, in connection with the communication module 203, may also be used to detect one or more impacts sustained by a user. For example, the data collection module 205 can detect the one or more impacts from sensor information derived from the sensor devices 109 (e.g., a sensor-based helmet, a sensor-based mouth guard, or a combination thereof). In one embodiment, it is contemplated that the communication module 203 enables the data collection module 205 to detect the one or more impacts via one or more short range wireless communications including Bluetooth®, NFC, or a combination thereof. Further, the data collection module 205 also may be used to monitor the one or more impacts sustained by a user over a period of time (e.g., the duration of a season).

In one embodiment, the calculation module 209 is used to calculate a severity level for a single one, a plurality, or an entirety of the one or more impacts. By way of example, the calculation module 209 can determine both the linear impact as well as the rotational movement or angular acceleration caused by the one or more impacts based on data collected by the data collection module 205. In particular, the calculation module 209 can calculate the severity level from sensor information collected from the data collection module 205 including g-force data, vibration data, acceleration data, rotational data, or a combination thereof. In one embodiment, the calculation module 209, in connection with the analysis module 211, further calculates the severity level of the one or more impacts by comparing the severity level of the one or more impacts against impact threshold criteria stored in the impact database 105 and/or available via the networks 111-117 (e.g., a cloud service).

In one embodiment, the analysis module 211 is used to generate a recommendation for a level of participation of a user, one or more other users, or a combination thereof in a team activity based on the one or more impacts, a severity level of the one or more impacts, or a combination thereof. In one example use case, the analysis module 211 receives the calculated severity level for the one or more impacts from the calculation module 209 via the communication module 203 and then compares the severity level against one or more recommendations stored in the impact database 105, for example. Based on the comparison, the analysis module 211 can then generate the appropriate recommendation. For example, the one or more recommendations may include "remove the user for the rest of the activity," "carefully monitor the user's performance for a period of time," "examine the user for possible signs of a concussion," "the user is safe to participate and/or to continue participating," etc. In one embodiment, it is contemplated that the analysis module 211 can predict a level of risk of short-term and/or long-term injury for a user based on the one or more impacts sustained by the user over a period of time. For example, the analysis module 211 may predict that a user that has sustained a high number of impacts during a season, for example, may be at a moderate to high level or risk to injury despite the fact that the impacts sustained by the user were minimal or moderate in severity.

In one embodiment, the analysis module 211 may also be used to determine a substitution of a user by one or more other users participating in a team activity based on the one or more impacts. For example, the analysis module 211 can determine one or more substitutions based on the premise that there should be no users participating in the activity associated with the recommendation "remove the user for the rest of the activity" and as few as possible users participating in the activity associated with a recommendation "carefully monitor the user's performance for a period of time." Therefore, the analysis module 211 recommends substituting such users with one or more users associated with the recommendation "the user is safe to participate and/or continue participating."

In one embodiment, the rendering module 213 is used to present a recommendation, a representation of the severity level, a representation of the level of participation, or a combination thereof in a user interface (e.g., a user interface of a user device 101 such as a mobile phone, a phablet, and/or a tablet). By way of example, the rendering module 213 can present the recommendation in the form of text (e.g., "remove the user from for the rest of the activity), one or more audio and/or haptic alerts (e.g., a vibration immediately after a user sustains one or more severe impacts), one or more color representations (e.g., red for "at risk," yellow for "proceed with caution," and green for "safe"), or a combination thereof.

In one embodiment, the storage module 215 is used to manage the storage of the number and/or severity level of the one or more impacts sustained by one or more users participating in a team activity over a period of time, biometric and/or contextual data associated with the one or more users, or a combination thereof in the impact database 105. The storage module 215 may also be used to manage the storage of the one or more recommendations for a level of participation for a user, one or more users, or a combination thereof participating in a team activity.

Figure 3:
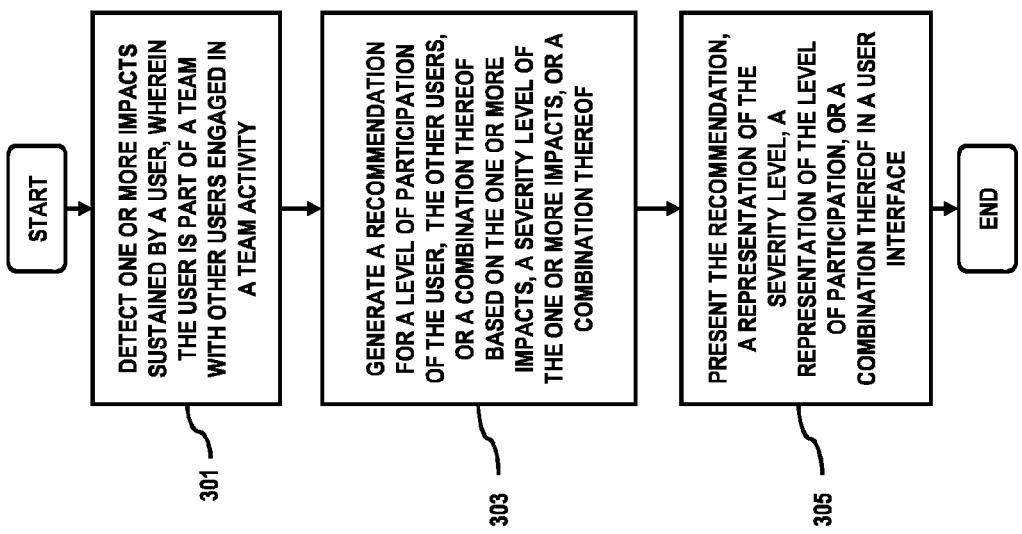
FIGS. 3-5 are flowcharts of processes for providing diagnostic information regarding one or more impacts sustained by one or more users while the one or more users are participating in a team activity, according to various embodiments.
Figure 4:
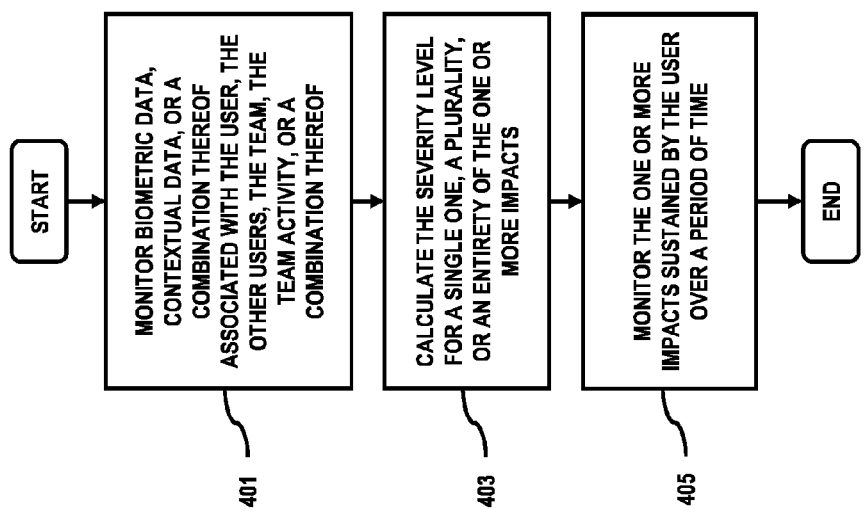
Figure 5:
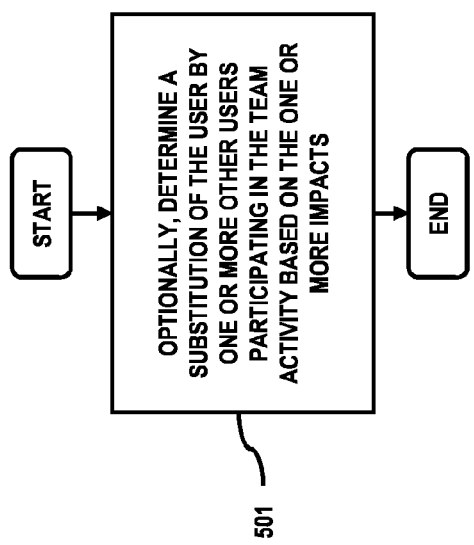
Figure 8:
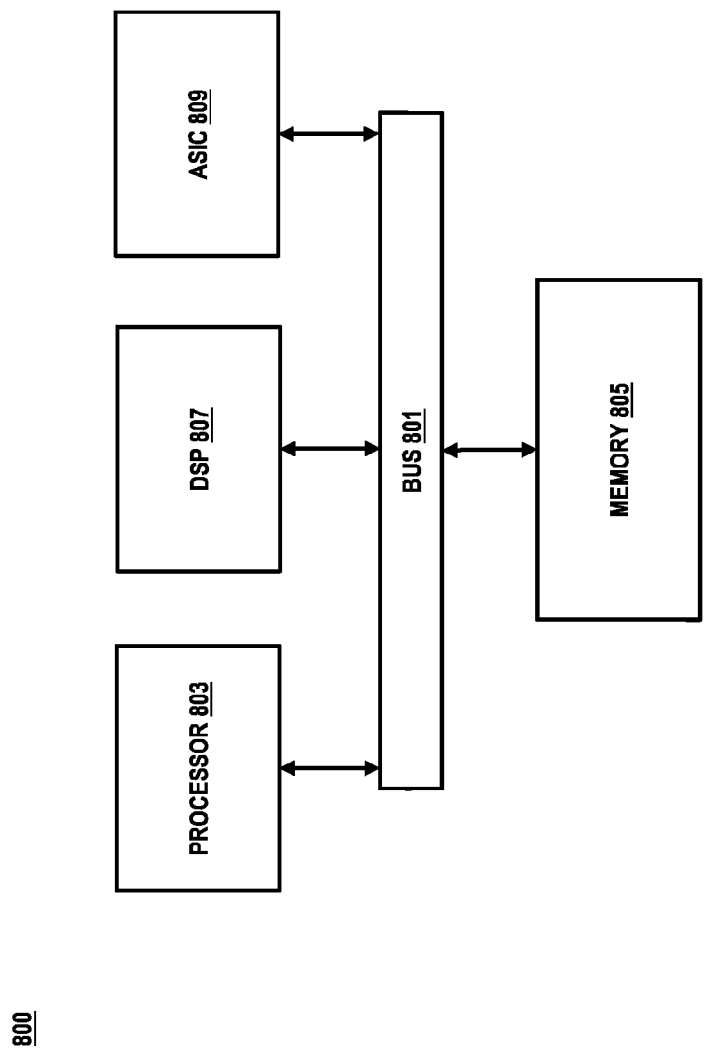
FIG. 8 is a diagram of a chip set that can be used to implement an embodiment of the invention.

FIGS. 3-5 are flowcharts of processes for providing diagnostic information regarding one or more impacts sustained by one or more users while the one or more users are participating in a team activity, according to various embodiments. In one embodiment, the diagnostic platform 103 performs the process 300 and is implemented in, for instance, a chip set including a processor and a memory as shown in FIG. 8. In step 301, the diagnostic platform 103 detects one or more impacts sustained by a user, wherein the user is part of a team with one or more other users engaged in a team activity. By way of example, the one or more impacts may include linear, rotational, and/or angular movement of a user's brain. In particular, the measure of the movement is collected from sensor information associated with equipment worn by the user, the one or more other users, or a combination thereof (e.g., a sensor-based helmet, a sensor-based mouth guard, or a combination thereof) and the sensor information includes, g-force data, vibration data, acceleration data, rotational data, or a combination thereof. For example, a user may be a football player that sustains a single severe impact (e.g., a mild traumatic brain injury or a concussion—knocking him or her out of the activity) or the user may sustain a number of impacts throughout the course of the activity, a season, a career, or a combination thereof. By way of further example, the team activity is a physical activity or contact sport in which impact to one's head may likely occur.

In step 303, the diagnostic platform 103 generates a recommendation for a level of participation of the user, the one or more other users, or a combination thereof in the team activity based on the one or more impacts, a severity level of the one or more impacts, or a combination thereof. By way of example, the diagnostic platform 103 generates the recommendation by comparing the number of the one or more impacts, the calculated severity of the one or more impacts, or a combination thereof sustained by a user over a period of time (e.g., the duration of the activity or the duration of a season) against one or more corresponding recommendations stored in the impact database 105, for example. In addition, the diagnostic platform 103 can generate the recommendation based on the biometric and/or contextual data associated with a user and stored in the impact database 105, for example. Further, in one embodiment, it is contemplated that the diagnostic platform 103 can predict a level of risk of short-term and/or long-term injury for a user based on the one or more impacts sustained by a user over a period of time and can then generate a recommendation for a level of participation for the user accordingly. For example, based on one or more impacts sustained by a user (e.g., user "A"), the diagnostic platform 103 can recommend to a coach, for example, that the user should not continue to participate in the activity for the duration of the activity or the duration of the season (e.g., if the user has already sustained a number of severe impacts over the course of the season and/or his or her career depending on the particular circumstances). In addition and alternatively, the diagnostic platform 103 can recommend to a coach, for example, that the user should be carefully watched for a period of time and/or examined by medical personnel (e.g., a clinician, a trainer, etc.) for possible signs of a mild traumatic brain injury or a concussion. Further, the diagnostic platform 103 can also recommend that the user is safe to participate and/or to continue participating in the activity despite having sustained one or more impacts (e.g., one or more impacts of minimal severity). By way of further example, the diagnostic platform 103 can generate the recommendation for a level of participation for a user in substantially real-time, periodically, according to a schedule, on demand, or a combination thereof.

In step 305, the diagnostic platform 103 presents the recommendation, a representation of the severity level, a representation of the level of participation, or a combination thereof in a user interface. By way of example, the presentation of the recommendation may include visual, audio, and/or haptic alerts in connection with one or more user devices (e.g., a mobile phone, a phablet, a tablet, etc.). In one embodiment, it is contemplated that the diagnostic platform 103 can present a text-based recommendation (e.g., "take the user off the field for the rest of the activity) and/or a color-based recommendation (e.g., a red representation of the user) in the user interface of the one or more user devices. For example, a coach may be able to view one or more users on the team participating in the activity in substantially-real team based on one or more color gradations depending on the one or more impacts, the severity of the one or more impacts, or a combination thereof sustained by the one or more users on the team. In one example use case, a user that has sustained a number of impacts and/or a severe impact recently may be represented as a red color, a user that has sustained a number of impacts of minimal severity may be represented as a yellow color, and a user that has not sustained any impacts or has sustained only a few impacts of minimal severity may be represented as a green color. By way of further example, the presentation may include one or more audio and/or haptic alerts (e.g., a vibration immediately after a user sustains a severe impact).

FIG. 4 depicts a process 400 of generating a recommendation for a level of participation of a user. In one embodiment, the diagnostic platform 103 performs the process 400 and is implemented in, for instance, a chip set including a processor and a memory as shown in FIG. 8. In step 401, the diagnostic platform 103 monitoring biometric data, contextual data, or a combination thereof associated with the user, the one or more other users, the team, the team activity, or a combination thereof, wherein the recommendation is further based on the biometric data, the contextual data, or a combination thereof. By way of example, the biometric data may include height, weight, athletic condition, etc. associated with one or more users. By way of further example, the contextual data may include the medical history of a user (e.g., any pre-existing conditions, one or more previously sustained impacts, etc.), an amount of elapsed time since previously sustaining one or more impacts, weather conditions (e.g., temperature, rain, snow, etc.), drills or plays where one or more impacts are likely (e.g., tackling drills), specific positions within an activity (e.g., a running back versus a quarterback in football), location on the body where one or more impacts have been sustained, etc. In one embodiment, it is contemplated that a user, a coach, or medical personnel (e.g., a clinician, a trainer, etc.) can input the biometric data, contextual data, or a combination thereof into the diagnostic platform 103 via a user device 101 (e.g., a tablet) before the user starts participating in a team activity and thereby establishing one or more baseline values for the user; during the team activity to monitor any changes; or a combination thereof. In one embodiment, depending on the sophistication of the one or more user devices 101, the one or more sensor devices 109 (e.g., a sensor-based helmet), some of the contextual data (e.g., time and temperature) may be automatically uploaded to the diagnostic platform 103 via the networks 111-117 (e.g., a cloud service) and therefore not require manual input on the part of the user, the coach, and/or medical personnel.

In step 403, the diagnostic platform 103 calculates the severity level for a single one, a plurality, or an entirety of the one or more impacts, wherein the recommendation is further based on comparing the severity level against impact threshold criteria, wherein the recommendation is further based on comparing the severity level against impact threshold criteria. By way of example, the diagnostic platform 103 calculates the severity level by comparing the sensor information including g-force data, vibration data, acceleration data, rotational data, or a combination thereof against impact threshold criteria (e.g., a concussion grading system and/or clinical studies) stored in the impact database 105 and/or available via the networks 111-117 (e.g., a cloud service). For example, the diagnostic platform 103 can determine that a user sustained an impact consisting of a linear impact component (e.g., x number of g's) and/or a rotational movement or angular acceleration component (e.g., x number radians/s$^2$) and determine that based on those values compared against the impact threshold criteria that the user has sustained a concussion.

In step 405, the diagnostic platform 103 monitors the one or more impacts sustained by the user over a period of time, wherein the recommendation specifies the level of participation for at least a portion of the period of time. In one embodiment it is completed that the period of time represents a duration of the team activity, a duration of a season for a team activity, a duration of a career for the team activity, or a combination thereof.

FIG. 5 depicts an optional process 500 of presenting a recommendation for a level of participation for one or more users of a team participating in a team activity. In one embodiment, the diagnostic platform 103 performs the process 500 and is implemented in, for instance, a chip set including a processor and a memory as shown in FIG. 8. In step 501, the diagnostic platform 103 optionally determines a substitution of the user by the one or more other users participating in the team activity based on the one or more impacts, wherein the recommendation includes the substitution. By way of example, if the diagnostic platform 103 detects that a user (e.g., user "A") has sustained one or more impacts and that the one or more impacts are severe, the diagnostic platform 103 can recommend to a coach, for example, a substitution of another user (e.g., user "B") for user "A" while the activity is ongoing and/or for a period of time (e.g., the next scheduled activity). In one embodiment, it is contemplated that the diagnostic platform 103 can determine the one or more substitutions based on the premise that there should be no users participating in the activity associated with the recommendation "remove the user for the rest of the activity" and as few users as possible participating in the activity associated with the recommendation "carefully monitor the user's performance for a period of time" and that any such users should be substituted, if possible, with users that are associated with the recommendation "the user is safe to participate and/or to continue participating."

FIGS. 6A-6D are diagrams of user interfaces utilized in the processes of FIGS. 3-5, according to various embodiments. As shown, the example user interfaces of FIGS. 6A-6C include one or more user interface elements and/or functionalities created and/or modified based, at least in part, on information, data, and/or signals resulting from the processes (e.g., 300, 400, and 500) described with respect to FIGS. 3-5. More specifically, FIGS. 6A-6D illustrate a user interface 601 of a user device (e.g., a mobile phone) depicting an impact status of one or more users engaged in a team activity (e.g., football). In one embodiment, it is contemplated that the user interface 601 is connected to one or more sensor devices (e.g., a sensor based-helmet, a sensor-based mouth guard, or a combination thereof)(not shown for illustrative convenience) via one or more short range wireless communications including Bluetooth®, NFC, or a combination thereof.

Figure 6A:
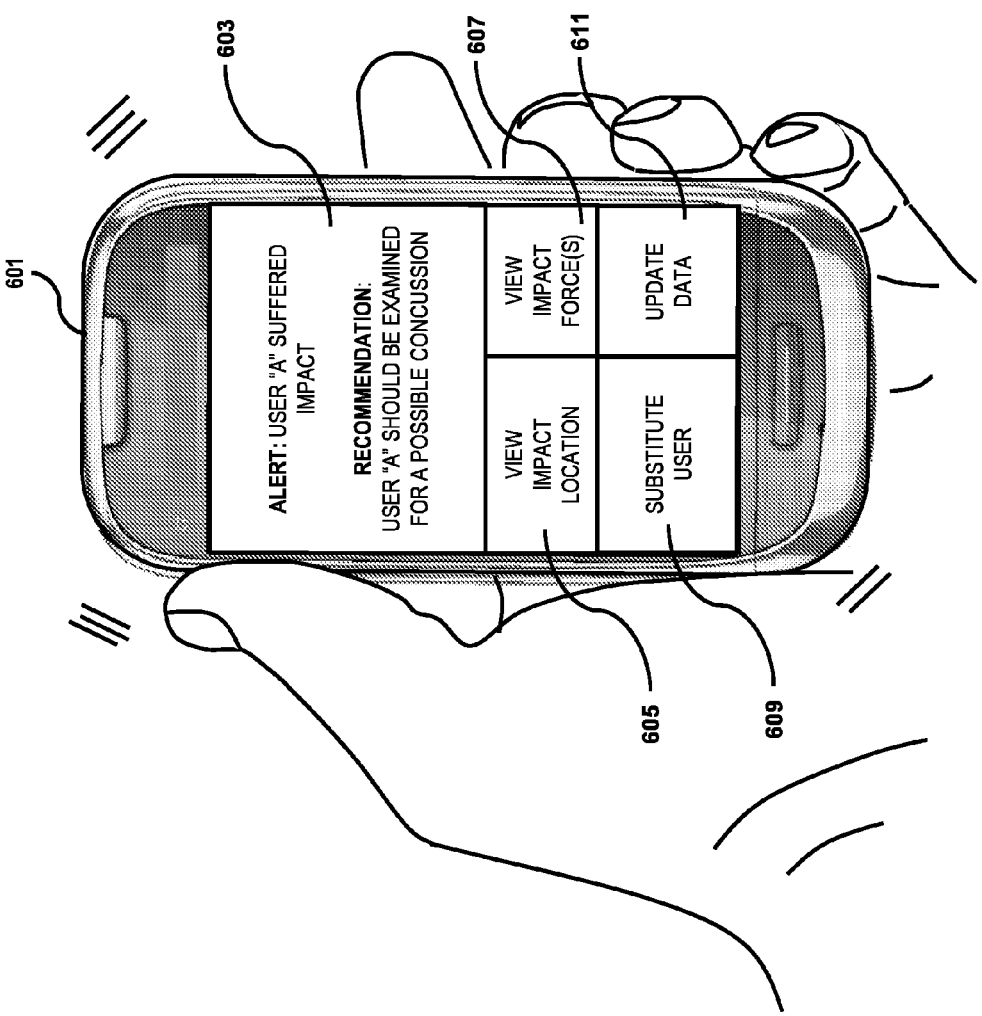
FIGS. 6A-6D are diagrams of user interfaces utilized in the processes of FIGS. 3-5, according to various embodiments.

By way of example, FIG. 6A depicts the user interface 601 presenting a recommendation, a representation of a severity level, a representation of a level of participation, or a combination thereof of one or more impacts sustained by a user engaged in team activity (e.g., football). For example, in this example use case, the system 100 detects one or more impacts sustained by a user (e.g., user "A") during a football game, for example. In one embodiment, the system 100 detects the one or more impacts sustained by user "A" based on sensor information (e.g., g-force data, vibration data, acceleration data, rotational data, or a combination thereof) detected from one or more sensor devices worn by user "A" (e.g., a sensor-based helmet and/or a sensor-based mouth guard). In one embodiment, the system 100 calculates the severity of the impact by comparing the measure of the linear and/or angular acceleration sustained by user "A" against impact threshold criteria (e.g., a concussion grading scale and/or clinical studies). As a result of the detection and calculation by the system 100, in one embodiment, the system 100 generates a recommendation for a level of participation for user "A" (e.g., "user 'A' should be examined for a possible concussion"). In one embodiment, the system 100 presents a text-based recommendation 603 to a coach or medical personnel, for example, in the user interface 601 and the user interface vibrates as well. In one embodiment, the user interface 601 may also include interactive elements 605 and 607 that can be used by a coach or medical personnel (e.g., an emergency room doctor) to view the specific location of the one or more impacts (e.g., a text-based or graphical-based description) and/or view the specific impact forces (e.g., as g's and/or as radians/$s^2$) sustained by user "A", for example, to further qualitatively analyze the one or more impacts sustained by the user. In addition, in one embodiment, the user interface 601 may also include an interactive element 609 that can be used by a coach, for example, to determine a substitution and an interactive element 611 that can be used by a user, a coach, and/or medical personnel to update the user's contextual data (e.g., store a record of the recent impact in the impact database 105, for example).

Figure 6B:
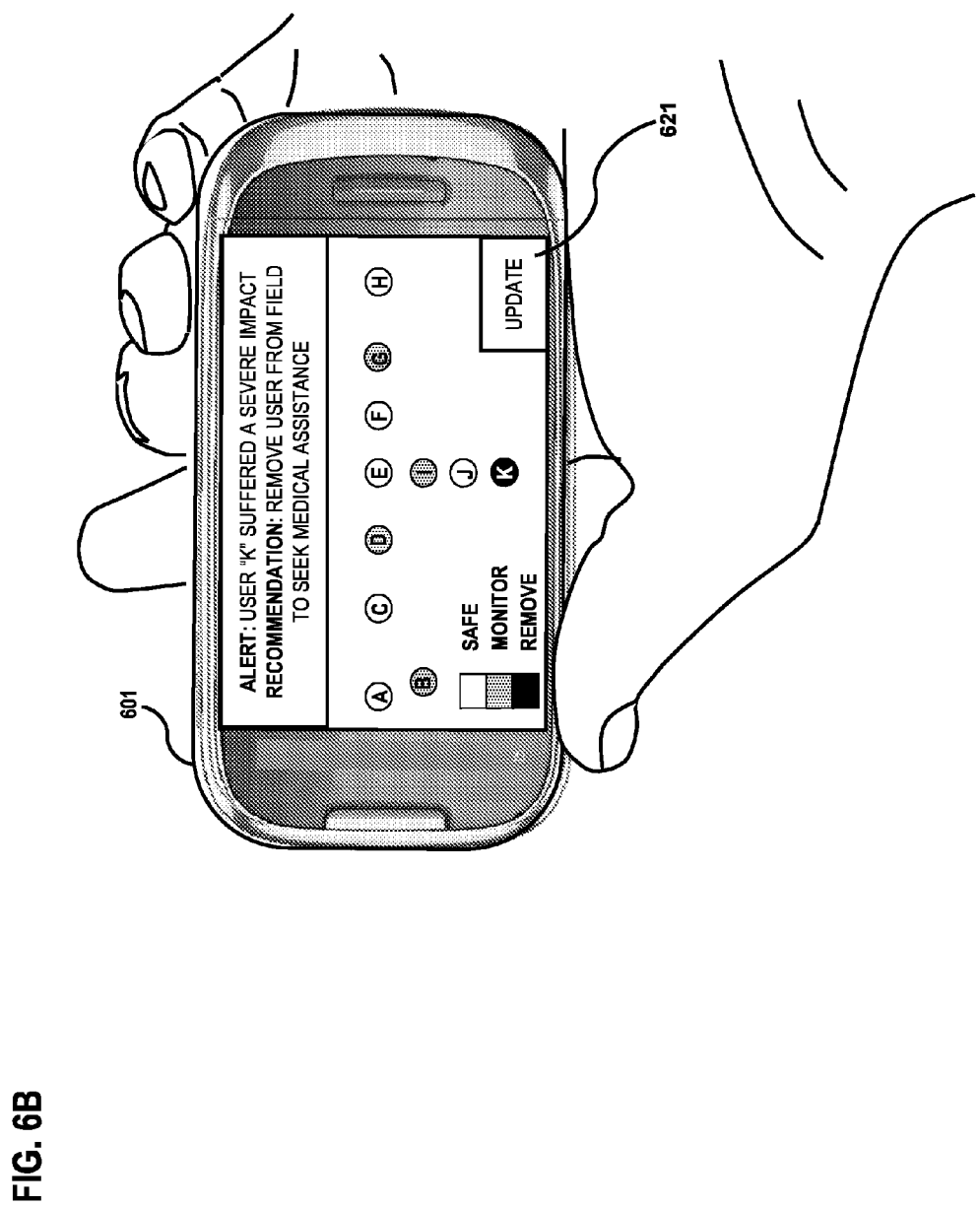
Figure 6C:
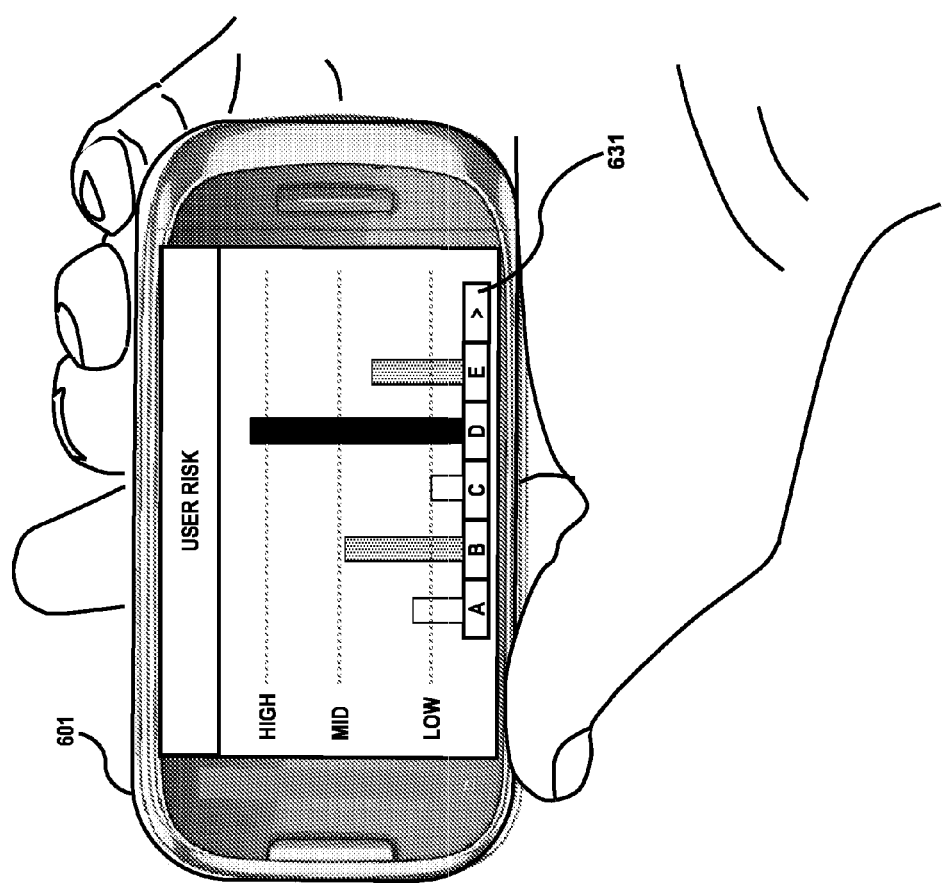

In one embodiment, the system 100 can present a recommendation for a level of participation for each of one or more users engaged in a team activity at the same time as depicted in FIG. 6B. More specifically, in this example use case, the system 100 has already detected the one or more impacts, if any, sustained by the one or more users and has calculated the severity level for each of the one or more impacts. Consequently, in one embodiment, the system 100 generates a recommendation for a level of participation for the one or more users participating in the team activity (e.g., football) based on the one or more impacts, a severity level of the one or more impacts, or a combination thereof. In one embodiment, the system 100 presents the recommendation, a representation of the severity level, a representation of the level of participation, or a combination thereof in the user interface 601. For example, in this example use case, the system 100 has detected that user "K" has sustained at least one severe impact and has recommended that user "K" be removed from the field to seek medical attention. In addition, the system 100 has detected that users "B", "D", "G", and "I" have sustained one or more impacts and has calculated that the severity level of the one or more impacts is sufficient to recommend that the coach or medical personnel, for example, monitor the users over a period of time (e.g., the next few plays). Further, the system 100 has detected that users "A", "C", "E", "F", "H", and "J" have either not sustained any impacts and/or that the one or more impacts that the respective users have sustained were not severe enough to warrant a cautionary recommendation. As previously discussed, in one embodiment, it is contemplated that the system 100 can generate the recommendation in substantially-real time, periodically, according to a schedule, on demand (e.g., via the interactive element 621), or a combination thereof In one embodiment, the system 100 can present a predicted level of risk of short-term and/or long term injury for a user (e.g., user's "A", "B", "C", "D", and "E") in interface 601 based on the one or more impacts sustained by each user over a period of time (e.g., a duration of an activity or a duration of a season) and can then generate a recommendation for a level of participation for the user as depicted in FIG. 6C. For example, in this example use case, the system 100 predicts that users "A" and "C" are at a low level of risk and therefore the system 100 recommends to a coach, for example, that the users are safe to participate and/or to continue participating in an activity. In contrast, the system 100 predicts that users "B" and "E" are at a moderate level of risk and therefore the system 100 recommends to the coach that the user's should be carefully monitored for a period of time and/or immediately examined upon sustaining one or more impacts. Further, the system 100 predicts that user "D" is at a high level of risk (e.g., user "D" has already sustained a considerable number of impacts over the course of the season even if those impacts were minimal or moderate in severity) and therefore the system 100 recommends preventing the user from participating in the activity for a period of time. In one embodiment, it is contemplated that a user interface element 631, for example, can enable a coach, for example, to view additional users on the team or participating in the activity and/or enable a user (e.g., a coach) to make one or more comparisons of risk (e.g., based on a particular position within an activity).

Figure 6D:
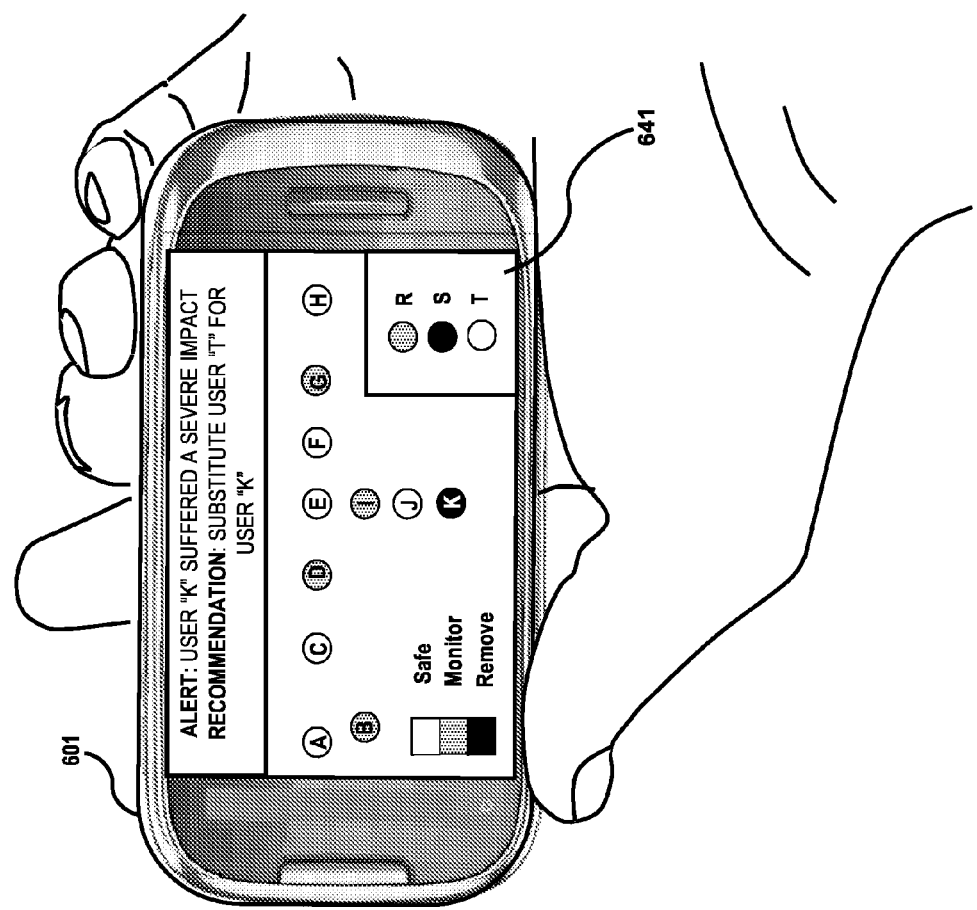

In one embodiment, the system 100 can determine a substitution of a user by one or more other users participating in a team activity based on the one or more impacts sustained by the one or more users as depicted in FIG. 6D. For example, continuing with the example use case depicted in FIG. 6B, the system 100 detected and calculated that user "K" sustained a severe impact and should be removed from the field to seek medical attention. As a result, in one embodiment, the system 100 can recommend that a coach, for example, substitute user "K" for one of the available players identified in the box 641 (e.g., users "R" and "T"). More specifically, in one embodiment, it is contemplated that the system 100 may determine the one or more substitutions based on the premise that there should be no "remove" users participating in the activity at any given time and that the number of "monitor" users participating in the activity should be minimized as much as possible. Therefore, in this example use case, the system 100 can determine to substitute user "T" for user "K" to maximize the number of "safe" or healthy users participating in the activity. Again, in one embodiment, the user interface 601 may include an interactive update element (e.g., element 621 of FIG. 6B) so that the most up-to-date information is available to a coach, for example, for making one or more substitutions.

Figure 7:
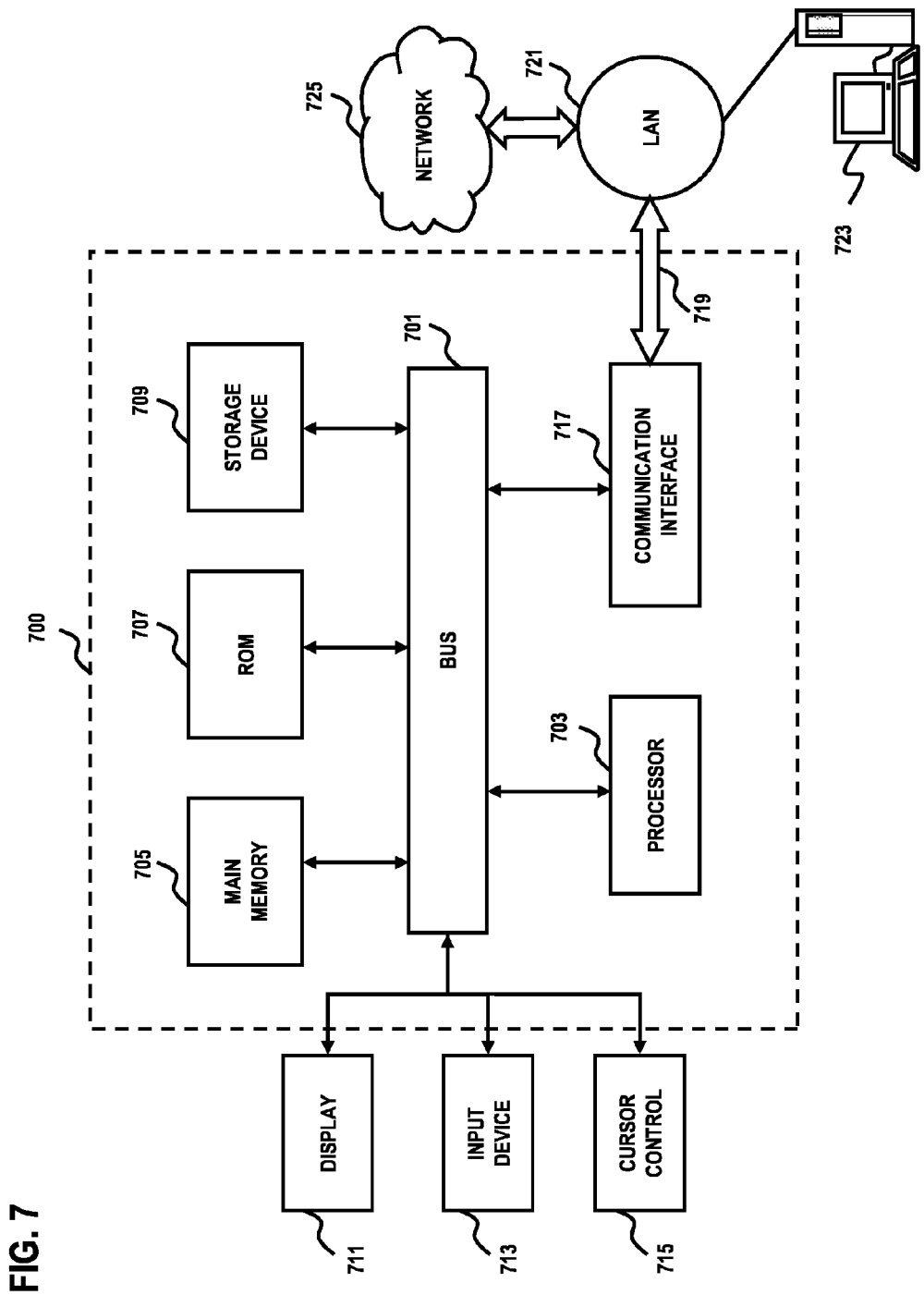
FIG. 7 is a diagram of a computer system that can be used to implement various exemplary embodiments.

FIG. 7 is a diagram of a computer system that can be used to implement various exemplary embodiments. The computer system 700 includes a bus 701 or other communication mechanism for communicating information and one or more processors (of which one is shown) 703 coupled to the bus 701 for processing information. The computer system 700 also includes main memory 705, such as a random access memory (RAM) or other dynamic storage device, coupled to the bus 701 for storing information and instructions to be executed by the processor 703. Main memory 705 can also be used for storing temporary variables or other intermediate information during execution of instructions by the processor 703. The computer system 700 may further include a read only memory (ROM) 707 or other static storage device coupled to the bus 701 for storing static information and instructions for the processor 703. A storage device 709, such as a magnetic disk or optical disk, is coupled to the bus 701 for persistently storing information and instructions.

The computer system 700 may be coupled via the bus 701 to a display 711, such as a cathode ray tube (CRT), liquid crystal display, active matrix display, or plasma display, for displaying information to a computer user. An input device 713, such as a keyboard including alphanumeric and other keys, is coupled to the bus 701 for communicating information and command selections to the processor 703. Another type of user input device is a cursor control 715, such as a mouse, a trackball, or cursor direction keys, for communicating direction information and command selections to the processor 703 and for adjusting cursor movement on the display 711.

According to an embodiment of the invention, the processes described herein are performed by the computer system 700, in response to the processor 703 executing an arrangement of instructions contained in main memory 705. Such instructions can be read into main memory 705 from another computer-readable medium, such as the storage device 709. Execution of the arrangement of instructions contained in main memory 705 causes the processor 703 to perform the process steps described herein. One or more processors in a multiprocessing arrangement may also be employed to execute the instructions contained in main memory 705. In alternative embodiments, hard-wired circuitry may be used in place of or in combination with software instructions to implement the embodiment of the invention. Thus, embodiments of the invention are not limited to any specific combination of hardware circuitry and software.

The computer system 700 also includes a communication interface 717 coupled to bus 701. The communication interface 717 provides a two-way data communication coupling to a network link 719 connected to a local network 721. For example, the communication interface 717 may be a digital subscriber line (DSL) card or modem, an integrated services digital network (ISDN) card, a cable modem, a telephone modem, or any other communication interface to provide a data communication connection to a corresponding type of communication line. As another example, communication interface 717 may be a local area network (LAN) card (e.g. for Ethernet™ or an Asynchronous Transfer Model (ATM) network) to provide a data communication connection to a compatible LAN. Wireless links can also be implemented. In any such implementation, communication interface 717 sends and receives electrical, electromagnetic, or optical signals that carry digital data streams representing various types of information. Further, the communication interface 717 can include peripheral interface devices, such as a Universal Serial Bus (USB) interface, a PCMCIA (Personal Computer Memory Card International Association) interface, etc. Although a single communication interface 717 is depicted in FIGS. 6A-6D, multiple communication interfaces can also be employed.

The network link 719 typically provides data communication through one or more networks to other data devices. For example, the network link 719 may provide a connection through local network 721 to a host computer 723, which has connectivity to a network 725 (e.g. a wide area network (WAN) or the global packet data communication network now commonly referred to as the "Internet") or to data equipment operated by a service provider. The local network 721 and the network 725 both use electrical, electromagnetic, or optical signals to convey information and instructions. The signals through the various networks and the signals on the network link 719 and through the communication interface 717, which communicate digital data with the computer system 700, are exemplary forms of carrier waves bearing the information and instructions.

The computer system 700 can send messages and receive data, including program code, through the network(s), the network link 719, and the communication interface 717. In the Internet example, a server (not shown) might transmit requested code belonging to an application program for implementing an embodiment of the invention through the network 725, the local network 721 and the communication interface 717. The processor 703 may execute the transmitted code while being received and/or store the code in the storage device 709, or other non-volatile storage for later execution. In this manner, the computer system 700 may obtain application code in the form of a carrier wave.

The term "computer-readable medium" as used herein refers to any medium that participates in providing instructions to the processor 703 for execution. Such a medium may take many forms, including but not limited to computer-readable storage medium ((or non-transitory)—i.e., non-volatile media and volatile media), and transmission media. Non-volatile media include, for example, optical or magnetic disks, such as the storage device 709. Volatile media include dynamic memory, such as main memory 705. Transmission media include coaxial cables, copper wire and fiber optics, including the wires that comprise the bus 701. Transmission media can also take the form of acoustic, optical, or electromagnetic waves, such as those generated during radio frequency (RF) and infrared (IR) data communications. Common forms of computer-readable media include, for example, a floppy disk, a flexible disk, hard disk, magnetic tape, any other magnetic medium, a CD-ROM, CDRW, DVD, any other optical medium, punch cards, paper tape, optical mark sheets, any other physical medium with patterns of holes or other optically recognizable indicia, a RAM, a PROM, and EPROM, a FLASH-EPROM, any other memory chip or cartridge, a carrier wave, or any other medium from which a computer can read.

Various forms of computer-readable media may be involved in providing instructions to a processor for execution. For example, the instructions for carrying out at least part of the embodiments of the invention may initially be borne on a magnetic disk of a remote computer. In such a scenario, the remote computer loads the instructions into main memory and sends the instructions over a telephone line using a modem. A modem of a local computer system receives the data on the telephone line and uses an infrared transmitter to convert the data to an infrared signal and transmit the infrared signal to a portable computing device, such as a personal digital assistant (PDA) or a laptop. An infrared detector on the portable computing device receives the information and instructions borne by the infrared signal and places the data on a bus. The bus conveys the data to main memory, from which a processor retrieves and executes the instructions. The instructions received by main memory can optionally be stored on storage device either before or after execution by processor.

FIG. 8 illustrates a chip set or chip 800 upon which an embodiment of the invention may be implemented. Chip set 800 is programmed to provide diagnostic information regarding one or more impacts sustained by one or more users while the one or more users are participating in a team activity as described herein and includes, for instance, the processor and memory components described with respect to FIG. 7 incorporated in one or more physical packages (e.g., chips). By way of example, a physical package includes an arrangement of one or more materials, components, and/or wires on a structural assembly (e.g., a baseboard) to provide one or more characteristics such as physical strength, conservation of size, and/or limitation of electrical interaction. It is contemplated that in certain embodiments the chip set 800 can be implemented in a single chip. It is further contemplated that in certain embodiments the chip set or chip 800 can be implemented as a single "system on a chip." It is further contemplated that in certain embodiments a separate ASIC would not be used, for example, and that all relevant functions as disclosed herein would be performed by a processor or processors. Chip set or chip 800, or a portion thereof, constitutes a means for performing one or more steps of providing diagnostic information regarding one or more impacts sustained by one or more users while the one or more users are participating in a team activity.

In one embodiment, the chip set or chip 800 includes a communication mechanism such as a bus 801 for passing information among the components of the chip set 800. A processor 803 has connectivity to the bus 801 to execute instructions and process information stored in, for example, a memory 805. The processor 803 may include one or more processing cores with each core configured to perform independently. A multi-core processor enables multiprocessing within a single physical package. Examples of a multi-core processor include two, four, eight, or greater numbers of processing cores. Alternatively or in addition, the processor 803 may include one or more microprocessors configured in tandem via the bus 801 to enable independent execution of instructions, pipelining, and multithreading. The processor 803 may also be accompanied with one or more specialized components to perform certain processing functions and tasks such as one or more digital signal processors (DSP) 807, or one or more application-specific integrated circuits (ASIC) 809. A DSP 807 typically is configured to process real-world signals (e.g., sound) in real time independently of the processor 803. Similarly, an ASIC 809 can be configured to performed specialized functions not easily performed by a more general purpose processor. Other specialized components to aid in performing the inventive functions described herein may include one or more field programmable gate arrays (FPGA) (not shown), one or more controllers (not shown), or one or more other special-purpose computer chips.

In one embodiment, the chip set or chip 800 includes merely one or more processors and some software and/or firmware supporting and/or relating to and/or for the one or more processors.

The processor 803 and accompanying components have connectivity to the memory 805 via the bus 801. The memory 805 includes both dynamic memory (e.g., RAM, magnetic disk, writable optical disk, etc.) and static memory (e.g., ROM, CD-ROM, etc.) for storing executable instructions that when executed perform the inventive steps described herein to provide diagnostic information regarding one or more impacts sustained by one or more users while the one or more users are participating in a team activity. The memory 805 also stores the data associated with or generated by the execution of the inventive steps.

While certain exemplary embodiments and implementations have been described herein, other embodiments and modifications will be apparent from this description. Accordingly, the invention is not limited to such embodiments, but rather to the broader scope of the presented claims and various obvious modifications and equivalent arrangements.

Further, to the extent the aforementioned embodiments collect, store or employ personal information provided by individuals, it should be understood that such information shall be used in accordance with all applicable laws concerning protection of personal information. Additionally, the collection, storage and use of such information may be subject to consent of the individual to such activity, for example, through well known "opt-in" or "opt-out" processes as may be appropriate for the situation and type of information. Storage and use of personal information may be in an appropriately secure manner reflective of the type of information, for example, through various encryption and anonymization techniques for particularly sensitive information.

What is claimed is:

1. A method comprising:
   detecting one or more impacts sustained by a user, wherein the user is part of a team with one or more other users engaged in a team activity;
   determining a substitution of the user by the one or more other users participating in the team activity based on the one or more impacts;
   generating a recommendation for a level of participation of the user in the team activity based on the one or more impacts, a severity level of the one or more impacts, or a combination thereof, wherein the recommendation includes the substitution; and presenting the recommendation, a representation of the severity level, a representation of the level of participation, or a combination thereof in a user interface.

2. A method of claim 1, further comprising:
monitoring the one or more impacts sustained by the user over a period of time,
wherein the recommendation specifies the level of participation of at least a portion of the period of time.

3. A method of claim 2, wherein the period of time represents a duration of the team activity, a duration of a season of the team activity, a duration of a career of the team activity, or a combination thereof.

4. A method of claim 1, further comprising:
monitoring biometric data, contextual data, or a combination thereof associated with the user, the one or more other users, the team, the team activity, or a combination thereof,
wherein the recommendation is further based on the biometric data, the contextual data, or a combination thereof.

5. A method of claim 1,
wherein the substitution includes disengaging the user from the team activity.

6. A method of claim 1, further comprising:
calculating the severity level of a single one, a plurality, or an entirety of the one or more impacts,
wherein the recommendation is further based on comparing the severity level against impact threshold criteria.

7. A method of claim 6, wherein the severity level is based on sensor information collected from equipment worn by the user, the one or more other users, or a combination thereof.

8. A method of claim 7, wherein the sensor information includes g-force data, vibration data, acceleration data, rotational data, or a combination thereof.

9. An apparatus comprising:
at least one processor; and
at least one memory including computer program code for one or more programs,
the at least one memory and the computer program code configured to, with the at least one processor, cause the apparatus to perform at least the following,
detect one or more impacts sustained by a user, wherein the user is part of a team with one or more other users engaged in a team activity,
determine a substitution of the user by the one or more other users participating in the team activity based on the one or more impacts,
generate a recommendation of a level of participation of the user in the team activity based on the one or more impacts, a severity level of the one or more impacts, or a combination thereof,
wherein the recommendation includes the substitution, and
present the recommendation, a representation of the severity level, a representation of the level of participation, or a combination thereof in a user interface.

10. An apparatus of claim 9, wherein the apparatus is further configured to:
monitor the one or more impacts sustained by the user over a period of time,
wherein the recommendation specifies the level of participation of at least a portion of the period of time.

11. An apparatus of claim 10, wherein the period of time represents a duration of the team activity, a duration of a season of the team activity, a duration of a career of the team activity, or a combination thereof.

12. An apparatus of claim 9, wherein the apparatus is further configured to:
monitor biometric data, contextual data, or a combination thereof associated with the user, the one or more other users, the team, the team activity, or a combination thereof,
wherein the recommendation is further based on the biometric data, the contextual data, or a combination thereof.

13. An apparatus of claim 9,
wherein the substitution includes disengaging the user from the team activity.

14. An apparatus of claim 9, wherein the apparatus is further configured to:
calculate the severity level of a single one, a plurality, or an entirety of the one or more impacts,
wherein the recommendation is further based on comparing the severity level against impact threshold criteria.

15. An apparatus of claim 14, wherein the severity level is based on sensor information collected from equipment worn by the user, the one or more other users, or a combination thereof.

16. An apparatus of claim 15, wherein the sensor information includes g-force data, vibration data, acceleration data, rotational data, or a combination thereof.

17. A system comprising:
a diagnostic platform configured to detect one or more impacts sustained by a user, wherein the user is part of a team with one or more other users engaged in a team activity; determine a substitution of the user by the one or more other users participating in the team activity based on the one or more impacts; generate a recommendation of a level of participation of the user in the team activity based on the one or more impacts, a severity level of the one or more impacts, or a combination thereof, wherein the recommendation includes the substitution; and present the recommendation, a representation of the severity level, a representation of the level of participation, or a combination thereof in a user interface.

18. A system of claim 17, further comprising:
the diagnostic platform further configured to monitor the one or more impacts sustained by the user over a period of time,
wherein the recommendation specifies the level of participation of at least a portion of the period of time,
wherein the substitution includes disengaging the user from the team activity.

19. A system of claim 18, wherein the period of time represents a duration of the team activity, a duration of a season of the team activity, a duration of a career of the team activity, or a combination thereof.

20. A system of claim 17, further comprising:
the diagnostic platform further configured to monitor biometric data, contextual data, or a combination thereof associated with the user, the one or more other users, the team, the team activity, or a combination thereof,
wherein the recommendation is further based on the biometric data, the contextual data, or a combination thereof.

* * * * *